United States Patent
Odidi et al.

(10) Patent No.: US 10,159,649 B2
(45) Date of Patent: *Dec. 25, 2018

(54) CONTROLLED RELEASE DELIVERY DEVICE COMPRISING AN ORGANOSOL COAT

(71) Applicant: Intellipharmaceutics Corp., Mississauga, Ontario (CA)

(72) Inventors: Isa Odidi, Toronto (CA); Amina Odidi, Toronto (CA)

(73) Assignee: INTELLIPHARMACEUTICS CORPORATION, Toronto (CA)

(*) Notice: Subject to any disclaimer, the term of this patent is extended or adjusted under 35 U.S.C. 154(b) by 101 days.

This patent is subject to a terminal disclaimer.

(21) Appl. No.: 15/399,010

(22) Filed: Jan. 5, 2017

(65) Prior Publication Data

US 2017/0112770 A1    Apr. 27, 2017

Related U.S. Application Data

(60) Division of application No. 12/225,954, filed on Apr. 6, 2009, now Pat. No. 9,561,188, which is a
(Continued)

(51) Int. Cl.
*A61K 9/20* (2006.01)
*A61K 31/137* (2006.01)
(Continued)

(52) U.S. Cl.
CPC .......... *A61K 9/2054* (2013.01); *A61K 9/0053* (2013.01); *A61K 9/167* (2013.01);
(Continued)

(58) Field of Classification Search
CPC ................ A61K 9/2054; A61K 31/137; A61K 31/4458; A61K 9/0053; A61K 9/2009;
(Continued)

(56) References Cited

U.S. PATENT DOCUMENTS

2003/0068371 A1  4/2003  Oshlack et al.
2003/0118641 A1  6/2003  Maloney et al.
(Continued)

OTHER PUBLICATIONS

European Office Action dated Jul. 6, 2018 for European application No. 07 719 784.6.
(Continued)

*Primary Examiner* — Trevor Love
(74) *Attorney, Agent, or Firm* — Ohlandt, Greeley, Ruggiero & Perle, LLP

(57) ABSTRACT

A controlled release delivery device for controlled release of an active ingredient comprising: (i) a core particle comprising the active ingredient homogenously dispersed or dissolved therein; and (ii) an organosol polymeric coat comprising a homogenous mixture of, (a) a water soluble gel forming polymer and a water insoluble organosoluble polymer in a dry weight ratio of from about 20:80 to about 50:50, (b) an organosolvent, and (c) an anti-tacking agent; the organosol polymeric coat being applied directly to and substantially enveloping the core particle.

28 Claims, 1 Drawing Sheet

Mean Profile: water 24 hrs

Related U.S. Application Data continuation-in-part of application No. 11/396,166, filed on Apr. 3, 2006.

(51) Int. Cl.
| | | |
|---|---|---|
| *A61K 31/4458* | (2006.01) | |
| *A61K 9/00* | (2006.01) | |
| *A61K 31/4525* | (2006.01) | |
| *A61K 9/28* | (2006.01) | |
| *A61K 31/192* | (2006.01) | |
| *A61K 31/138* | (2006.01) | |
| *A61K 9/16* | (2006.01) | |
| *A61K 9/24* | (2006.01) | |

(52) U.S. Cl.
CPC .......... *A61K 9/1611* (2013.01); *A61K 9/1623* (2013.01); *A61K 9/1652* (2013.01); *A61K 9/209* (2013.01); *A61K 9/2009* (2013.01); *A61K 9/2013* (2013.01); *A61K 9/2018* (2013.01); *A61K 9/2077* (2013.01); *A61K 9/2095* (2013.01); *A61K 9/282* (2013.01); *A61K 9/2846* (2013.01); *A61K 9/2853* (2013.01); *A61K 9/2866* (2013.01); *A61K 9/2886* (2013.01); *A61K 31/137* (2013.01); *A61K 31/138* (2013.01); *A61K 31/192* (2013.01); *A61K 31/4458* (2013.01); *A61K 31/4525* (2013.01); *Y02A 50/411* (2018.01)

(58) Field of Classification Search
CPC ................ A61K 9/2013; A61K 9/2018; A61K 31/4525; A61K 9/2095; A61K 9/282; A61K 9/2853; A61K 31/192; A61K 31/138; A61K 9/1611; A61K 9/2886; A61K 9/2866; A61K 9/2846; A61K 9/209; A61K 9/2077; A61K 9/167; A61K 9/1652; A61K 9/1623; Y02A 50/411
See application file for complete search history.

(56) References Cited

U.S. PATENT DOCUMENTS

| | | | |
|---|---|---|---|
| 2004/0131669 A1* | 7/2004 | Kerc | A61K 9/0065 424/454 |
| 2006/0003007 A1 | 1/2006 | Odidi et al. | |
| 2006/0024361 A1 | 2/2006 | Odidi et al. | |
| 2006/0039864 A1 | 2/2006 | Bartholomaus | |

OTHER PUBLICATIONS

Canadian Office Action dated Sep. 29, 2017 for Canadian application No. 2,648278.

Buhse et al; "Topical Drug Classification"; International Journal of Pharmaceutics 295, 1-2; 2005; pp. 101-112.

Canadian Office Action dated Dec. 7, 2016 for Canadian application No. 2,648278.

* cited by examiner

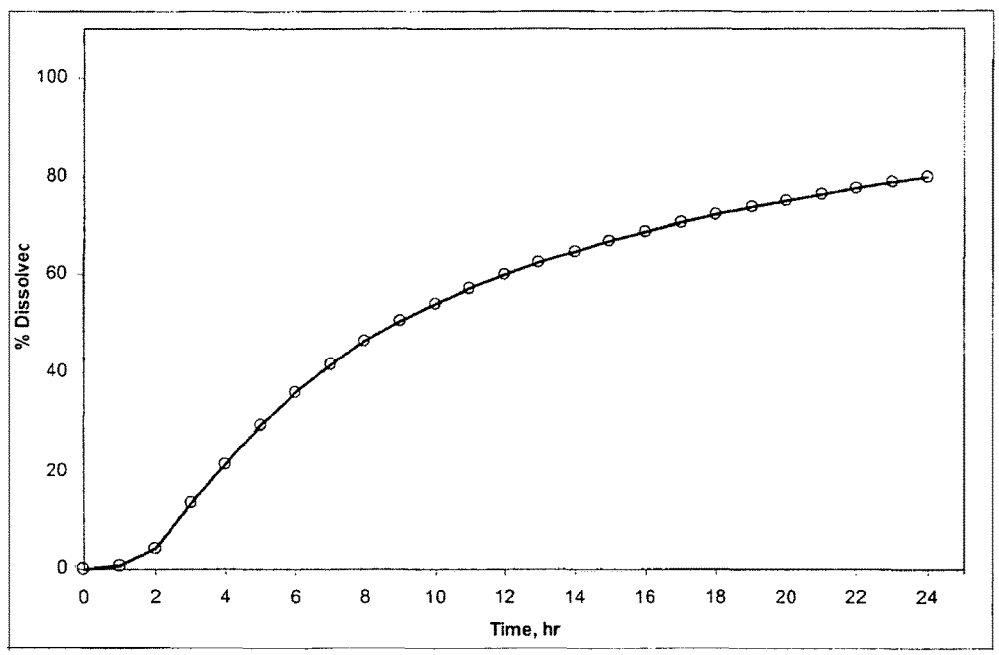
Mean Profile: water 24 hrs

CONTROLLED RELEASE DELIVERY DEVICE COMPRISING AN ORGANOSOL COAT

CROSS-REFERENCED APPLICATIONS

The present application is a Divisional application of U.S. patent application Ser. No. 12/225,954, filed on Apr. 6, 2009, which is a Continuation-in-Part of U.S. patent application Ser. No. 11/396,166, filed Apr. 3, 2006, all of which are incorporated in their entirety by reference thereto.

FIELD OF THE INVENTION

The present invention relates to a device for the controlled delivery of active ingredient(s). The present invention also relates to the use and method for making the same.

BACKGROUND OF THE INVENTION

Many pharmaceutical oral dosage forms for sustained release of drugs are taught in the prior art. Some of these are in form of swellable matrices in which drug release is via tortuous channels controlled by a swelling polymer. Some are reservoir systems in which drug release is via a laser drilled pin hole controlled by osmotic pressure. While some are beads surrounded by a coat impregnated with soluble materials in which drug release is via channels created by the dissolution of the soluble materials. Coats have been used as means to control the site of release of an active ingredient.

U.S. Pat. No. 6,946,146 teaches a coating composition for coating a solid dosage form of a medicament having at least 50% (w/w) by dry weight of a water insoluble polymer insoluble in both acidic, basic and neutral pH, present in the form of an aqueous latex dispersion and a water soluble component present in a weight ratio of about 5 to about 50% (w/W) by dry weight of the coating, the water soluble component being organic and either solid or liquid and said water soluble component being selected from the group consisting of polydextrose, polyalcohol or ester of polyalcohol, a non-polymeric sugar, a non-polymeric sugar alcohol and amino acid, and the ratio of water insoluble polymer to water soluble component ranging from about 95:5 to about 1:1. The solid content in the coating composition ranging from about 5% to about 25%. As discussed below, inherent disadvantages exist in the use of aqueous latex dispersion of water insoluble polymer for coating.

U.S. Pat. No. 6,911,217 teaches a controlled release bead comprising (i) a core unit of a substantially water-soluble or water-swellable inert material; (ii) a first layer on the core unit of a substantially water-insoluble polymer; (iii) a second layer covering the first layer and containing an active ingredient; and (iv) a third layer of polymer on the second layer effective for controlled release of the active ingredient, wherein the first layer is adapted to control water penetration into the core. This approach is complicated by the core requiring protection from water throughout manufacture.

U.S. Pat. No. 6,902,742 describes a multiparticulate modified release composition comprising a first population of active ingredient-containing particles and at least one subsequent population of active ingredient-containing particles, the active ingredient contained in the first population being an opiate and the active ingredient in the subsequent population being an opiate or a non-opiate, wherein the subsequent population of active ingredient-containing particles further comprises a modified release coating or, alternatively or additionally, a modified release matrix material, such that the composition following oral delivery to a subject delivers the active ingredients of the first and subsequent populations in a pulsatile manner. A problem with matrix formulated material is that it is susceptible to dose dumping under feed conditions and a burst effect under fasted conditions.

U.S. Pat. No. 6,251,432 describes a dosage form for delivery of one or more beneficial agents into a fluid, such as liquid enteral nutritional product. The dosage form unit includes a core containing at least one beneficial agent, preferably a marker dye, which is dispersible in the fluid. A latex coating encases the core. The latex coating includes a mixture containing a substantially hydrophobic base material, preferably formed from an emulsion of cellulose acetate microspheres, which is capable of defining a matrix-type membrane, and at least one hydrophilic component being dispersible in the fluid. A dispersible beneficial agent is preferred as one of the hydrophilic components of the latex coating to allow immediate release of the beneficial agent therefrom. Problems with latex coating compositions are discussed below. Furthermore, matrix type membranes are susceptible to dose dumping under feed conditions and a burst effect under fasted conditions.

U.S. Pat. No. 6,022,562 relates to microcapsules for the oral administration of medicinal and/or nutritional active principles, which are smaller than or equal to 1000 micrometers in size and consist of particles which are coated with a coating material consisting of a mixture of a film-forming polymer derivative, a hydrophobic plasticizer, a functional agent and a nitrogen-containing polymer.

U.S. Pat. No. 5,840,335 describes a system for the controlled release of an active agent and is made of a core surrounded by a shell made of a wall formed of a water-insoluble material which is permeable to the passage of an external fluid. The core is comprised of a water soluble active agent and a soluble polymeric adjuvant, such as polyvinyl alcohols, and a cellulose compound such as methyl cellulose, methylethylcellulose, hydroxypropylcellulose, hydroxypropylmethyl cellulose and carboxymethyl cellulose, capable of unlimited swelling. Placing swelling materials in the core complicates the manufacturing process.

U.S. Pat. No. 5,783,215 discloses controlled release beads where each bead comprises (i) a core unit of a soluble or insoluble inert material, (ii) a first layer on the core unit comprising an active ingredient dispersed in a hydrophilic polymer, (iii) an optional second layer of hydrophilic polymer covering the first layer, and (iv) an outermost membrane layer effective for controlled release of the active ingredient. The core is not used to contain the drug and therefore lower amounts of the drug are typically loaded in this form.

U.S. Pat. No. 5,759,577 discloses a compressed medicinal tablet comprising a tablet core and a sugar coating, where the sugar contains a dose of a hormonal steroid, a drug and a steroid release rate controlling amount of microcrystalline cellulose, and PVP to aid in application of the sugar coat. The sugar coating technique is time consuming and prone to variability.

U.S. Pat. No. 5,736,159 discloses a controlled release pharmaceutical tablet. This system is based on a core which contains a water soluble osmotic agent, a water-swellable pharmaceutically acceptable polymer and surrounded by a membrane coating made essentially of a modified water insoluble polymer and a water soluble polymer. Inclusion of osmotic agent and swellable polymer complicates manufacturing as the core must be protected from water.

U.S. Pat. No. 5,595,762 describes stabilized pulverulent active agents, compositions made by coating with a coating composition comprising at least one film-forming agent, in proportions of between 2 and 25% by weight of the final mass, and at least one pore-forming agent, in proportions of between 0 and 5% by weight of the final mass.

U.S. Pat. No. 5,458,887 discloses a controlled release dosage form consisting of an osmotic core comprising essentially of a drug and water swellable component selected from the group consisting of hydroxypropylmethyl cellulose and polyethylene oxide wherein the core is surrounded with a coat comprising of a water resistant polymer and a minor amount of a non-toxic water soluble pharmaceutically acceptable compound (e.g., salt crystals) in an amount which is sufficient to dissolve in the gastrointestinal fluid and form a plurality of micropores on the outside of the tablet, the water resistant polymer being microporus to the passage of the gastrointestinal fluid. Drug release is via the passage way created when the water soluble salt crystals is dissolved in contact with the aqueous medium.

U.S. Pat. No. 5,376,388 describes a water soluble drug core surrounded by a hydratable diffusion barrier made of a film-forming polymer such as an acrylic resin or ethyl cellulose and an additive which controls the rate of hydration and permeability of the hydratable diffusion barrier selected from the group consisting of fully esterified acrylic resins containing quaternary amine side chains, lubricant anionic surfactants, plasticizers, inert water soluble materials and mixtures thereof. The present invention does not teach the use of a hydratable diffusion barrier made from esterified acrylic resins and drug release is not controlled by the rate of hydration of the coating.

U.S. Pat. No. 5,126,146 discloses a microporous, cellulosic coating useful in combination with osmotically controlled drug delivery devices. The coating composition consist essentially of a single layer surrounding a core compartment comprising: a latex derived from an aqueous colloidal dispersion of a cellulosic polymer, surfactant, plasticizer and a pore-forming agent selected from the group consisting of urea, dimethyl sulfone, nicotinamide, or an amino acid.

U.S. Pat. No. 4,966,768 describes a sustained release oral dosage form made by compressing an active ingredient plus a high molecular weight hydroxypropylmethylcellulose, methyl cellulose, sodium carboxymethylcellulose and or other cellulose ether. The dosage form in '768 is a matrix system and is subject to dose dumping especially when taken with food.

U.S. Pat. No. 4,963,365 describes a controlled release dosage form which consists essentially of a core containing a medicament; an inner coating layer composed of ethylcellulose and a hydrophobic substance; and an outer coating layer containing a medicament are also disclosed. This dosage form uses only water insoluble substances for its inner coating layer and relies solely on an outer coating layer containing a medicament to obtain the required loading dose for rapid increase in blood concentration of the medicament.

U.S. Pat. Nos. 4,886,668 and 4,880,631 directed to osmotic pumps, for the controlled release of an active substance, teach a core surrounded by a rate controlling water insoluble wall as coat which utilizes a polymer permeable to water but impermeable to solute and a pH insensitive pore forming additive dispersed through the wall.

U.S. Pat. No. 4,765,989 describe an osmotic system comprising a wall comprising, in at least a part, of a semipermeable material that surrounds a compartment. The compartment contains an osmotic composition and drug, and a second and different osmotic composition. The drug is released with aid of osmotic tension via a passageway in the wall that connects the first osmotic composition with the exterior of the system.

U.S. Pat. No. 4,389,393 discloses sustained release therapeutic compressed solid unit dose forms of an active ingredient plus a carrier base comprised of a high molecular weight hydroxypropylmethylcellulose, methyl cellulose, sodium carboxymethylcellulose and or other cellulose ether. This system is subject to dose dumping especially when taken with food.

U.S. Pat. No. 4,330,338 ('338 patent) describes pharmaceutical coatings in the form of aqueous dispersions or latex preparation of a water insoluble polymer, such as ethyl cellulose. Tablet cores coated according to the '338 patent release active agent by diffusion, which can be an exceedingly slow process unless systems with a large surface area are utilized. To expedite release of active agent from tablets coated with, e.g., an ethyl cellulose coating prepared in accordance with the disclosure of the '338 patent, hydroxypropylmethylcellulose (HPMC) has been added to the coating. '338 further discloses that HPMC, enhances the water solubility of the ethyl cellulose coats, causing the coating and subsequently the tablet core to rapidly disintegrate in an environment of use such as the intestine. Such rapid disintegration, however, is unsuitable for those applications in which drug is to be delivered continuously over time such as those taught in the present invention.

U.S. Pat. No. 4,31,285 discloses an osmotic device having coat comprising an annealed subcoat and an overcoat, annealed at about 35 degree C. to 65 degree C. for 10 to 72 hours.

U.S. Pat. No. 4,248,856 disclose the use of sugar coating in conjunction with a barrier coating on a core containing medicament and the cellulose polymers hydroxypropyl methylcellulose and ethylcellulose in order to provide controlled release of pharmaceuticals.

U.S. Pat. No. 4,060,598 teaches a coated pharmaceutical tablet comprising a core of active material and at least one layer of a coating made up of a film forming aqueous synthetic resin dispersion (such as polyvinyl esters, polyacrylic acid esters, polyvinyl acetate, polyvinyl chloride or butadienestyrene copolymers) and a water or alkaline soluble material. It further describes the resulting coated tablet as a core surrounded by a continuous porous matrix of synthetic resin formed from the aqueous dispersion which is insoluble in water and insoluble in the gastrointestinal tract. '598 patent also describes the coating as achieving fast disintegrating or enteric disintegrating coating for tablets.

U.S. Pat. No. 4,016,880 describes a tablet having an osmotic material and a sustained release coating. The drug is released through passages in the coating caused by structural weaknesses.

Most of the controlled release technologies described in the prior art above have as a common feature, a rate controlling membrane surrounding a core which comprise of drug and controlled release polymer and/or an osmotic agent or in some cases the core contain no drug. In many of the aforementioned disclosures, the membrane is made from water insoluble polymers, and various additives are added in various forms to alter the permeability of the membrane to allow and control the rate of release of drug. Some of them require the presence of certain ingredients, e.g., osmotic ingredients, for the formulation to function.

The coating and core compositions described in the prior art have disadvantages. Sugar coating of a solid dosage has the drawback of being a very involved process requiring highly skilled operators and it has no application in controlled release drug delivery. The problem with osmotic devices is that they are tedious and difficult to fabricate. Their efficiency and precision is also in doubt as they have been known to break up prematurely or retain some of the drug content during transit in the gastrointestinal tract, which may lead to less drug being released and delivered by such devices. It is, therefore, not uncommon for such devices to contain an overage of drug of at least 10% to account for such inefficiencies in dose delivery. This practice is not economical and presents a danger, especially if potent drugs are used, as these devices have been known to rupture in transit thus releasing excess dose.

There has been a move towards aqueous coating systems such as aqueous based synthetic polymer dispersions which are produced by emulsion polymerization and latex dispersions. This is because these aqueous systems are nonflammable and thus provide no explosion hazard, is substantially free of toxic effects and is innocuous to the environment. However, the use of aqueous systems of polymers for film coating to provide dosage coatings has its draw backs, these systems are subject to bacterial and mold growth without the presence of a preservative agent and the presence of pore forming materials as suggested by the prior art may cause coalescence or coagulation of the latex dispersion, which may render it un-usable. These lattices also require the presence of surfactants in order to stabilize the latex dispersions from coalescence. Furthermore, in order to obtain a coating of uniform thickness and integrity there is need to subject the latex coated dosage form to a curing process by heating under high temperature. Latex dispersions have a high tacking factor, curing tends to result in an irreversible agglomeration of the dosage form and damage of the coating upon separation of the dosage forms. This results in a faster release than with uncured dosage forms.

Use of aqueous coating systems is complicated further by the slow evaporation of water and large amounts of water which must be removed from each coating. Further, many drugs are sensitive to water when exposed to high concentrations for extended periods of time and, accordingly, require initial sealing with water barriers.

The use of additives or soluble components in latex coating compositions as suggested in the prior art can lead to film instability during coating. Films formed with the addition of the soluble component are weaker than the film formed by using the insoluble polymer latex alone. This is because of the mechanisms by which latex films are deposited and formed around a substrate. The film is formed by the coalescence of the polymer latex particles. The presence of the water soluble component which is not soluble or physically compatible with the polymer would prevent complete coalescence of the polymeric particles and thus produces a weaker film. At high concentrations the water soluble component will help cause erosion of the film formed from latex systems. It is therefore critical that the water soluble component is soluble in water and the solubility is in excess of 5% (w/w). Latex systems are limited with regards to the amount of soluble and or swellable components that can be added to the system.

Therefore, there is still a need to develop a stable drug delivery device that can be reproducibly manufactured and have a desired effect of controlled release.

SUMMARY OF THE INVENTION

An object of an aspect of the present invention is to provide a delivery device to control the rate and extent of delivery of an active ingredient, for example, without limitation an active pharmaceutical ingredient, biological, chemical, nutraceutical, agricultural or nutritional active ingredients.

In accordance with an aspect of the present invention, there is provided a controlled release delivery device for controlled release of an active ingredient comprising: (a) a core particle comprising the active ingredient homogenously dispersed or dissolved therein; and (b) a polymeric coat comprising a water soluble gel forming polymer and a water insoluble organosoluble polymer, the polymeric coat being applied directly to and substantially enveloping the core particle.

In accordance with an aspect of the present invention, there is provided a controlled release delivery device for controlled release of an active ingredient comprising: (a) a core particle comprising the active ingredient homogenously dispersed or dissolved therein; and (b) a polymeric coat comprising a water soluble gel forming polymer and a water insoluble organosoluble polymer, the polymeric coat being applied directly to and substantially enveloping the core particle, wherein the core particle does not need to be protected from water.

In accordance with an aspect of the present invention, there is provided a controlled release delivery device for controlled release of an active ingredient comprising: (a) a core particle comprising the active ingredient homogenously dispersed or dissolved therein; and (b) a polymeric coat comprising a homogenous mixture of a water soluble gel forming polymer and a water insoluble organosoluble polymer in an organosolvent, the polymeric coat being applied directly to and substantially enveloping the core particle, wherein the polymeric coat does not comprise a latex dispersion.

In accordance with an aspect of the present invention, there is provided a controlled release delivery device for controlled release of an active ingredient comprising: (a) a core particle comprising the active ingredient homogenously dispersed or dissolved therein; and (b) a polymeric coat comprising a homogenous mixture of a water soluble gel forming polymer and a water insoluble organosoluble polymer in an organosolvent, the polymeric coat being applied directly to and substantially enveloping the core particle, wherein the polymeric coat does not comprise regions of pore forming agents.

In accordance with an aspect of the present invention, there is provided a controlled release delivery device for controlled release of an active ingredient comprising: (a) a core particle comprising the active ingredient homogenously dispersed or dissolved therein; and (b) a first polymeric coat comprising a homogenous mixture of a water soluble gel forming polymer and a water insoluble organosoluble polymer in an organosolvent, the first polymeric coat being applied directly to and substantially enveloping the core particle, wherein the first polymeric coat does not comprise a latex dispersion, a matrix-type membrane, or regions of pore forming agents, and the core particle does not comprise a swellable polymeric material.

In accordance with an aspect of the present invention, there is provided a controlled release delivery device for controlled release of an active ingredient comprising: (a) a core particle comprising the active ingredient homogenously dispersed or dissolved therein; and (b) a polymeric coat comprising a water soluble gel forming polymer and a water insoluble organosoluble polymer, the polymeric coat being applied directly to and substantially enveloping the core particle; wherein no water swellable polymeric material is present in the core; no latex dispersion is used for coating;

both the water insoluble organosoluble polymer and the water soluble gel forming polymer are present in an organosolvent in which it is homogeneously dispersed or dissolved; and the release of active ingredient from the core is controlled by the size and composition of the core as well as the surface area, and composition of the coat.

In accordance with an aspect of the present invention, there is provided a controlled release delivery device for controlled release of an active ingredient comprising: (a) a core particle comprising the active ingredient homogenously dispersed or dissolved therein; and (b) a polymeric coat comprising a homogenous mixture of a water soluble gel forming polymer and a water insoluble organosoluble polymer in an organosolvent, the polymeric coat being applied directly to and substantially enveloping the core particle, wherein the active ingredient is released from the formulation at a controlled rate such that therapeutically beneficial blood levels that are within a therapeutic window (below toxic levels and above minimum effective concentration) are achieved. These can be maintained over an extended period of time as desired, especially for less than 36 hours.

In accordance with an aspect of the present invention, there is provided a controlled release delivery device for controlled release of an active ingredient comprising:
(i) a core particle comprising the active ingredient homogenously dispersed or dissolved therein; and
(ii) an organosol polymeric coat comprising a homogenous mixture of, (a) a water soluble gel forming polymer and a water insoluble organosoluble polymer in a dry weight ratio of from about 20:80 to about 50:50, (b) an organosolvent, and (c) an anti-tacking agent;
the organosol polymeric coat being applied directly to and substantially enveloping the core particle.

In accordance with an aspect of the present invention, there is provided a controlled release delivery device for controlled release of an active ingredient comprising:
(i) a core particle comprising the active ingredient homogenously dispersed or dissolved therein; and
(ii) an organosol polymeric coat comprising a homogenous mixture of, (a) a water soluble gel forming polymer and a water insoluble organosoluble polymer in a dry weight ratio of from about 20:80 to about 50:50, (b) an organosolvent, and (c) an anti-tacking agent;
the organosol polymeric coat being applied directly to and substantially enveloping the core particle; wherein the organosol polymeric coat does not comprise a latex dispersion, a matrix-type membrane, or regions of pore forming agents, and the core particle does not comprise a swellable polymeric material in an amount sufficient to cause rupture or bursting of the organosol polymeric coat.

In accordance with another aspect of the present invention, there is provided a process for producing a controlled release delivery device for controlled release of an active ingredient comprising:
(i) providing a core particle comprising the active ingredient homogenously dispersed or dissolved therein;
(ii) applying an organosol polymeric coat comprising a homogenous mixture of,
   (a) a water soluble gel forming polymer and a water insoluble organosoluble polymer in a dry weight ratio of from about 20:80 to about 50:50,
   (b) an organosolvent, and
   (c) an anti-tacking agent; directly to the core particle to substantially envelope the core particle.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

BRIEF DESCRIPTION OF THE DRAWINGS

The following drawings are illustrative of embodiments of the invention and are not meant to limit the scope of the invention as encompassed by the claims.

FIG. 1 shows, in accordance with an embodiment of the invention, data regarding the release of an active pharmaceutical ingredient from a coated particle over a sustained-release period.

DETAILED DESCRIPTION OF THE INVENTION

The present invention relates to a novel composition and to a method of using and preparing same in order to control the rate and extent of delivery of an active ingredient. This is accomplished by the use of a homogenous polymeric coat comprising a water soluble gel forming polymer and a water insoluble organosoluble polymer. The active ingredient may be, without limitation, an active pharmaceutical ingredient; or biological, chemical, nutraceutical, agricultural or nutritional ingredients. The active ingredient may be in any suitable particle known in the art, for example, without limitation, granules, tablets, capsules, spheroids, pellets, microspheres, nanospheres, microcapsules, or crystals.

More specifically, the novel composition of the present invention can be used in any delivery device such as, and without being limited thereto, a sustained release, pulsed release, delayed release and/or controlled release device that controls the release of one or more active pharmaceutical ingredients. The device can be a solid unit dosage form. The device can be selected from, for example, one or more granules, one or more compressed tablets, one or more pellets and/or one or more capsules. In a specific embodiment, the device is a stable single homogeneous unit controlled release device which controls the release rate, without significant variability, and with a reproducible controlled release rate.

The composition may be administered in any suitable manner. For example and without being limited thereto, the composition can be in the form of a suitable device for in vivo oral, vaginal, anal, ocular, subcutaneous, intramuscular administration or for implantation. The composition may also be used for in vitro or ex vivo delivery of an active ingredient.

In one example, a non-rupturing controlled release delivery device for controlled release of an active ingredient comprises: (a) a core particle comprising the active ingredient homogenously dispersed therein; and (b) a polymeric coat comprising a water soluble gel forming polymer and a water insoluble organosoluble polymer, the polymeric coat being applied directly to and substantially enveloping the core particle.

The term "active ingredient" means any compound which has biological, chemical, or physiological utility including, without limitation, active pharmaceutical ingredient, drug, naturally occurring compound, nucleic acid compound, peptide compound, nutraceutical, agricultural or nutritional ingredient or synthetic drug.

The term "core particle" means a particle comprising an active ingredient and which is substantially surrounded or enveloped by a polymeric coating. The core particle can further comprise other compounds, including, without limitation, binders, buffers, antioxidants, fillers or other excipients. The core particle can be, without limitation, granules, tablets, capsules, spheroids, pellets, microspheres, nanospheres, microcapsules, crystals, or suitable mixtures thereof.

The terms "non-bursting" or "non-rupturing" or synonyms thereto mean that a coating of the core particle does not open or fly apart suddenly, as a result of internal pressure, in a manner that breaks, shatters, or explodes the integrity of the coating, thus exposing anything the coating had previously surrounded to the local environment.

The term "polymeric coating" or "polymeric coat" means any coating which is formed by polymerization of one or more monomers to form linear or branched or cross-linked macromolecules. The coating may be variously characterized as a coating, layer, membrane, shell, capsule, or the like, and substantially surrounds or envelope a core particle. Where a device of the present invention comprises more than one polymeric coat, a first polymeric coat substantially surrounds or envelopes a core particle, a second polymeric coat substantially surrounds or envelopes the first polymeric coat, and so forth. A subsequent (for example, second) polymeric coat may be applied to a previous (for example, first) polymeric coat in a contiguous or non-contiguous fashion. While second, third or further subsequent coats may take the form and composition of any known compatible controlled-release coat, for example a pH sensitive coat, a water repellant coat, or an aqueous solvent based coat, it will be understood that the first polymeric coat typically comprises a homogenous mixture of a water soluble gel forming polymer and a water insoluble organosoluble polymer in an organosolvent.

A polymeric coat prepared from a homogenous mixture comprising a water soluble gel forming polymer and a water insoluble organosoluble polymer in an organosolvent may be referred to as an "organosol polymeric coat". While the preparation of the first polymeric coat or the organosol polymeric coat is substantially non-aqueous, small amounts of water may be used or tolerated, for example, less than about 20% (v/v), less than about 10% (v/v), less than about 5% (v/v) or less than about 2% (v/v) of the polymeric coating composition before application to or incorporation into the controlled-release delivery device.

The term "organosolvent" means any organic solvent that is at least somewhat water soluble, having a Hildebrand Solubility Parameter of at least about 7.5 or 8 (Cal/cc).sup.1/2, usually at least about 9, more usually at least about 10. The organosolvent will have a dipole moment of at least about 1.5 D, usually at least about 2.0 D. One or more than one organosolvent may be used in the preparation of a polymeric coating composition. Typically, the organosolvent component of a polymeric coating composition will consist of one or two types of organosolvents, but may if desired consist of three, four or more organosolvents. The organosolvent component will make up the majority of the polymeric coating composition ranging from about 50 to 99.5% (v/v) of the composition, or from about 70 to 98% (v/v) of the composition, typically from about 75 to 97% (v/v) of the composition before application to or incorporation into the controlled-release delivery device. Organosolvents may be chosen such that any residual solvent that remains in an organosol polymeric coat does not result in an unacceptable systemic toxicity when a controlled-release delivery device comprising the organosol polymeric coat is administered or used to treat a subject or patient. When choosing organosolvents consideration may also be given to toxic effects that may be experienced by workers responsible for handling solvents in manufacturing or production of a controlled release delivery device. For example, methylene chloride is listed by the American Conference of Governmental industrial Hygienists as a potential carcinogen, as well as a potential cause of CNS depression, liver and kidney damage, and potential cause of elevated blood carboxyhemoglobin (also caused by exposure to carbon monoxide). Contact of the liquid with skin or eyes causes painful irritation and possible burns. Methylene chloride is considered an unsuitable organosolvent in the context of the present invention and will typically not be included in significant amounts in an organosolvent polymeric coating composition, for example less than 5%, or less than 4%, or less than 3%, or less than 2%, or less than 1% (v/v) based on the total volume of organosolvent used in preparation of an organosol polymeric coat. In certain examples, the amount of methylene chloride is less than or equal to a trace amount.

Examples of suitable organosolvents are described in U.S. Pat. No. 6,630,168 issued Oct. 7, 2003, titled "Gel delivery vehicles for anticellular proliferative agents". Suitable organosolvents may comprise Carbon, Nitrogen, Oxygen, Sulfur, Hydrogen and Phosphorus atoms, and may be cyclic or heterocyclic, and will generally be of low molecular weight, typically ranging from a molecular weight of greater than about 30 Da to a molecular weight of less than about 500 Da. Suitable organosolvents will generally have from 1 to 12 carbon atoms, or from 2 to 10 carbon atoms, and typically from 2 to 6 carbon atoms, and will comprise one or more heteroatoms (for example, N, O, S or P), typically no more than 8 heteroatoms.

Suitable organosolvents may comprise hydroxy heteroatoms including, for example and without limitation, lower alkanols of from 2 to 4 carbon atoms and 1 to 3 hydroxy groups, usually having no more than 1 hydroxy group for every 1.5 carbon atoms. Lower alkanols of interest include, without limitation, any one or any combination selected from ethanol, 1-propanol, 2-propanol, 1-propen-3-ol (allyl alcohol), propylene glycol, glycerol, 2-methyl-2-propanol, and the like. In certain examples, ethanol or anhydrous ethanol is used as the organosolvent. In another example, isopropanol is used as the organosolvent.

Suitable organosolvents may comprise amides that may be cyclic and include both N-substituted and unsubstituted amides, where any N-substituents will usually be alkyls of from 1 to 4 carbon atoms, more usually 1 to 3 carbon atoms. Particular amides of interest include, without limitation, any one or any combination selected from: formamide, methyl formamide, dimethyl formamide, ethyl formamide, diethyl formamide, acetamide, methyl acetamide, dimethyl acetamide, ethyl acetamide, diethyl acetamide. Cyclic amides (lactams) of interest include 2-pyrrolidone, N-methyl-2-pyrrolidone, N-ethyl-2-pyrrolidone. Ureas of interest include tetramethyl urea, 1,3-dimethyl-2-imidazolidinone, and the like.

Suitable organosolvents may comprise esters including, without limitation, esters of carboxylic acids as well as esters of inorganic acids. Examples of the former include triacetin, triethyl citrate, ethyl lactate, and the like. Examples of the latter include carbonate esters, where particular carbonate esters include: propylene carbonate, 1,2-butylene carbonate, 2,3-butylene carbonate and the like. Other suitable organosolvents include, for example and without limitation, dimethyl sulfoxide, diethyl sulfoxide, hexamethyl phosphoramide, pyruvic aldehyde dimethylacetal, dimethylisosorbide and the like.

A polymeric coat prepared from a homogenous mixture comprising a water soluble gel forming polymer and a water insoluble organosoluble polymer in a suitable organosolvent, for example, a lower alkanol allows for higher loading and a homogenous polymeric coat and typically allows for a better adhesion of the coat to a core particle compared to most aqueous coating systems. In certain examples, anhydrous ethanol is used as an organosolvent. With selection of an organosolvent such as a lower alkanol or anhydrous ethanol and use of modern coating techniques and explosion proof coating equipment, film coatings from organosols provide rapid, simple, effective coating of the solid dosage form and control over the dosage size, coating disintegration and dissolution rates, and generally results in an attractive, better and desirable dosage coating. Generally, the organosolvents curtailed bacterial and mold growth and surfactants may be optional, but are not required in the organosol polymeric coating composition used in the present invention.

The terms "sustained release", "pulsed release", "delayed release" and "controlled release" are used interchangeably in this application and are defined for purposes of the present invention as the release of an active ingredient from a delivery device at such a rate that when a dose of the active ingredient is administered in the sustained release, pulsed release, delayed release or controlled-release device, concentrations (levels) of the active ingredient are maintained within a desired range but below toxic levels over a selected period of time. In the case of in vivo administration, concentrations (levels) of the active ingredient could be measured in blood or plasma, for example. When administered in vivo the sustained release, pulsed release, delayed release or controlled-release device of the present invention allows for useful plasma concentration of an active ingredient to be maintained for longer than in the case of immediate-release forms.

In certain examples, in vitro dissolution testing shows a controlled release profile of less than 50% of an active ingredient is released in 1 hour, less than 80% is released in 6 hours and greater than 70% is released in 24 hours. In other examples, in vitro dissolution testing shows a controlled release profile of less than 60% of an active ingredient is released in 1 hour, less than 80% is released in 6 hours and greater than 70% is released in 24 hours. In other examples, in vitro dissolution testing shows a controlled release profile of greater than 20% of active ingredient is released in 24 hours. A suitable dissolution test is performed with a USP dissolution apparatus in water until an asymptote is reached and/or 24 hours has elapsed. Dissolution testing may also be performed with a USP dissolution apparatus at a acid media of pH 1.5 for 3 hours and the media being changed to phosphate buffer pH 7.5 until an asymptote is reached or 24 hours has elapsed. Other types of known dissolution tests may also be performed.

In general, the controlled release composition of the present invention do not have a tendency to (i) dose dump when taken under feed conditions, or (ii) produce a burst effect under fasted conditions. The extended release composition of the present invention may mitigate current incidences of untoward effects such as GI effects (e.g. nausea, vomiting), dizziness, and headache.

The controlled release profile may be modified on the basis of many factors pertaining to the polymeric coats, for example, without limitation, through the types of polymers used, the order in which they are deposited, the ratios of the polymers in the mix and the nature of their interaction. The controlled-release profile can also be modified by a variety of factors relating to the delivery device and the route of administration as outlined for example, in US Application No. 20070003619, published Jan. 4, 2007. For example, the sustained-release period will vary depending upon the solubility of the active ingredient, the rate of clearance of the active ingredient from the intended site of administration, the size of the core particle, the amount of the active ingredient initially present in the core particle, the presence of other compounds within the core particle that affect the rate of release of the active ingredient, the permeability of the polymeric coating(s) to the active pharmaceutical ingredient, and the rate of degradation of the polymeric coating(s), as well as other factors.

Release control may be effected or optimized through the types of polymers used, the order in which they are deposited, the number of polymeric coats, the width of polymeric coats, the ratios of the polymers in the mix and the nature of their interaction.

There are no specific restrictions as to the methods of manufacture of the composition, device or dosage form of the present invention. Typically, the device can be easily prepared, for instance, by the dry or wet granulation of an active ingredient. Optional components may be added such as, and without being limited thereto, silicone dioxide, one or more excipients, one or more oil components, and/or the like. The granules thus obtained are dried if required and passed through a mill and lubricated. The granules may be compressed into a shaped form in a rotary tablet press using a conventional method.

In certain examples granules, tablets, capsules, spheroids, pellets, microspheres, nanospheres, microcapsules, or crystals comprising an active ingredient can be prepared by wet or dry granulation, by extrusion spheronization, by powder or solution layering, by microencapsulation techniques, by milling and compression techniques. Coating may be carried out using fluid bed coating techniques or by coating using perforated side vented pan coating technique or by microencapsulation technique. These methods have been previously taught in the prior art.

In certain examples, different populations of coated particles can be packed together, for example, in a capsule or compressed into a tablet.

Methods of polymeric coating are well known in the art. For example, a core particle may be coated in a fluidized bed or pan, or by spraying or painting a polymeric coat onto a core particle. Another known option is a fluid bed bottom spray coater by having particles suspended in an air stream, and an aqueous dispersion of a polymeric coating composition is sprayed on to the particles. Various conventional coating apparatuses may be employed to facilitate this including, for example, a centrifugal fluidized bed coating apparatus, a pan coating apparatus, or a fluidized bed granulating coating apparatus.

In the preparation of the device, the device may be dryed at a predetermined temperature and relative humidity for a predetermined period of time in order to decrease or increase the rate of release of active ingredient(s) from the device. A drying process may also be carried out to simply remove a desired amount of solvent from the polymeric coat.

In the processes described herein, it is to be understood that during the coating of a core particle and/or after the core is completely coated, the solvent, for example water or alcohol, may be removed by techniques known to one of ordinary skill in the art such as by drying, and the like. As used herein, the term "coating" or "coat" or synonyms thereto includes both the process of applying the coating composition of the present invention to the core and the concomitant removal of the solvent, by techniques known to one of ordinary skill in the art, e.g., drying thereof in which substantially all of a solvent, for example water or alcohol, in the coating composition is removed. A controlled release delivery device of the present invention typically comprises an organosol polymeric coat prepared from a homogenous mixture comprising a water soluble gel forming polymer and a water insoluble organosoluble polymer in an organosolvent, the polymeric coat being applied directly to and substantially enveloping a core particle.

Water insoluble organosoluble polymers which are used in the present invention may be any polymers which are insoluble in water, are capable of being homogenously dissolved or dispersed in an organosolvent, and can typically retard the release of active ingredients. By the term "water-insoluble" is intended not susceptible to being dissolved (in water). Specific examples of water insoluble organosoluble polymers are, cellulose ether, cellulose ester, or cellulose ether-ester e.g., ethyl cellulose, acetyl cellulose, and nitrocellulose. Other water insoluble organosoluble polymers that can be used include acrylic and/or methacrylic ester polymers, polymers or copolymers of acrylate or methacrylate polyvinyl esters, polyvinyl acetates, polyacrylic acid esters, and butadiene styrene copolymers, and the like. Preferred water insoluble polymers are, ethylcellulose, cellulose acetate, polymethacrylates and aminoalkyl methacrylate copolymer.

In further specific examples, the acrylic polymer, includes, but is not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolyer, poly (methyl methacrylate), poly(methyl methacrylate) copolymer, polyacrylamide, aminoalkyl methacrylate copolymer, poly(methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The water insoluble polymers can be used either singly or in combinations of two or more.

Water soluble gel forming polymers which may be used in the present invention may be any polymers which are soluble in water, are capable of being homogenously dissolved or dispersed in an organosolvent, and can typically retard the release of active ingredients. Typically, the water soluble gel forming polymer is capable of hydrating quickly and forming strong, viscous gels. By the term "water-soluble" is intended susceptible of being dissolved (in water). Suitable water soluble gel forming polymers include those which can form hydrocolloid or can form a strong, viscous gel through which an active ingredient is released via diffusion or wicking. They include naturally occurring or synthetic, anionic or nonionic, hydrophilic rubbers, starch derivatives, cellulose derivatives, proteins, and the like. Specific non-limiting examples are gelatin, such as alginates, pectins, carrageenans, or xanthan; cellulose derivatives, such as methyl cellulose, hydroxypropylcellulose, hydroxyethylcellulose, hydroxypropyl methylcellulose, or sodium carboxymethylcellulose; starch and starch derivatives such as alpha starch or sodium carboxymethyl starch; galactomannan and galactomannan derivatives; polyvinylpyrrolidone, polyvinyl alcohol, vinyl-pyrrolidone-vinyl-acetate-copolymers, acacia, tragacanth, xanthan gum, locust bean gum, guar-gum, karaya gum, pectin, arginic acid, polyethylene oxide, Carbomer, polyethylene glycols, polypropylene glycols, carboxyvinyl polymer, sodium polyacrylate, albumin, dextrin, dextran sulfate, agar, gelatin, casein, sodium casein, pullulan, deacetylated chitosan, polyethyoxazoline, polyethylene oxide, poloxamers and the like. Of these, preferable are hydroxyethyl cellulose, hydroxypropyl methylcellulose, methylcellulose, hydroxypropyl cellulose, carbomer, polyethylene glycol, poloxamers, starch derivatives and polyvinylpyrrolidone. Water soluble gel forming polymers can be used either singly or in combinations of two or more. In an organosol polymeric coating composition a water soluble gel forming polymer may typically be present in an amount greater than 20% (w/w) of the water insoluble polymer on a dry weight basis.

The water soluble gel forming polymer may typically be added to an organosol polymeric coating composition in an amount from about 10 wt % to about 55 wt %; from about 10 wt % to about 50 wt %; from about 20 wt % to about 55 wt %; from about 20 wt % to about 50 wt %; from about 20 wt % to about 45 wt %; from about 20 wt % to about 40 wt %; from about 20 wt % to about 35 wt %; from about 25 wt % to about 55 wt %; from about 25 wt % to about 50 wt %; from about 25 wt % to about 45 wt %; from about 25 wt % to about 40 wt %; from about 25 wt % to about 35 wt %; or from about 30 wt % to about 50 wt %, on a dry weight basis of all components added to the coating composition excluding solvents. When further coats are added to the controlled release device, the water soluble gel forming polymer may typically be added to a coating composition according to known techniques, for example, in an amount from about 1 wt % to about 80 wt %; from about 1 wt % to about 70 wt %; from about 2 wt % to about 60 wt %; from about 3 wt % to about 50 wt %; or from about 4 wt % to about 45 wt %, on a dry weight basis.

The water insoluble organosoluble polymer may typically be added to an organosol polymeric coating composition in an amount from about 20 wt % to about 85 wt %; from about 20 wt % to about 75 wt %; from about 20 wt % to about 65 wt %; from about 20 wt % to about 55 wt %; from about 20 wt % to about 50 wt %; from about 20 wt % to about 45 wt %; from about 20 wt % to about 40 wt %; from about 25 wt % to about 75 wt %; from about 25 wt % to about 65 wt %; from about 25 wt % to about 55 wt %; from about 25 wt % to about 50 wt %; from about 25 wt % to about 45 wt %; or from about 30 wt % to about 50 wt % on a dry weight basis of all components added to the coating composition excluding solvents. When further coats are added to the controlled release device, the water insoluble organosoluble polymer may typically be added to a coating composition according to known techniques, for example, in an amount from about 1 wt % to about 90 wt %; from about 1 wt % to about 80 wt %; from about 1 wt % to about 70 wt %; from about 1 wt % to about 60 wt %; from about 1 wt % to about 50 wt %; from about 3 wt % to about 50 wt %; or from about 4 wt % to about 45 wt %.

The dry weight ratio of the water soluble gel forming polymer to the water insoluble organosoluble polymer in the organosol polymeric coat can be, typically, from about 10:90 to about 70:30, from about 10:90 to about 60:40, from about 10:90 to about 50:50, from about 10:90 to about 45:55, from about 10:90 to about 40:60, from about 20:80 to about 60:40, from about 20:80 to about 50:50, from about 20:80 to about 45:55, from about 20:80 to about 40:60, from about 25:75 to about 50:50, from about 25:75 to about 45:55, or from about 25:75 to about 40:60. When further coats are added to the controlled release device, the dry weight ratio of the water soluble gel forming polymer to the water insoluble organosoluble polymer may be set according to known techniques having regard, for example, to type of solvent (eg., aqueous, non-aqueous, or mixtures thereof) or the type of non-polymeric components (eg., hydrophobic or hydrophilic) or their relative amounts.

With respect to the coating composition, the coating composition, in certain examples, may comprise less than about 50 wt % of at least one water soluble gel forming polymer and less than about 50 wt % of at least one water insoluble organosoluble polymer. In specific examples, the coating composition may also comprise a plasticizer and an anti-tacking agent. For example, from about 1 wt % to about 80 wt % of at least one anti-tacking agent and about 1 wt % to about 80 wt % of at least one plasticizer may be used to make the coating composition.

In a specific embodiment, the coating composition comprises of from about 1 wt % to about 50 wt % of hydroxypropylmethylcellulose and from about 3 wt % to about 65 wt % of ethylcellulose.

While the controlled release delivery device of the present invention typically comprises an organosol polymeric coat comprising a homogenous mixture of a water soluble gel forming polymer and a water insoluble organosoluble polymer in an organosolvent, optional coats or components within a coat may be comprised of: hydrophobic or water repellant material such as oils, fats, waxes, higher alcohols; pH sensitive polymers; enteric polymers; or any other polymer, component or material known to be useful for preparing a controlled release coating.

The polymers used in the present invention may be pH insensitive or pH sensitive.

For a delivery device designed to be orally administered to the digestive tract, polymers that are known to be orally ingestible can be used and include, for example, polyvinyl alcohol, hydroxypropyl methyl cellulose, and other cellulose-based polymers. Other known polymers useful for enteral delivery include polymer materials which preferentially dissolve or disintegrate at different points in the digestive tract. Such polymers include, for example, the known acrylic and/or methacrylic acid-based polymers which are soluble in intestinal fluids, e.g. the Eudragit™ series of commercially available polymers. Examples of these include Eudragit E™, such as Eudragit E 100™ which preferentially dissolves in the more acid pH of the stomach, or enteric polymers such as Eudragit L™ and/or Eudragit S™ which preferentially dissolve in the more alkaline pH of the intestine, or polymers which dissolve slowly, e.g. a predetermined rate in the digestive tract, such as Eudragit RL™, e.g. Eudragit RL 100™, and/or Eudragit RS™ e.g. Eudragit R100™, and/or blends of such Eudragit™ polymers.

Hydrophobic or water repellant material that may be present in a coat is chosen from oil and fats, waxes, higher fatty acids, fatty acid esters, higher alcohols, hydrocarbons, and metal salts of higher fatty acids. Specific examples of oils and fats include plant oils, e.g. cacao butter, palm oil, Japan wax (wood wax), coconut oil, etc.; animal oils, e.g. beef tallow, lard, horse fat, mutton tallow, etc.; hydrogenated oils of animal origin, e.g. hydrogenated fish oil, hydrogenated whale oil, hydrogenated beef tallow, etc.; hydrogenated oils of plant origin, e.g. hydrogenated rape seed oil, hydrogenated castor oil, hydrogenated coconut oil, hydrogenated soybean oil, etc.; and the like. Of these hydrogenated oils are preferred as an oil component of the present invention.

Specific examples of waxes include plant waxes, e.g. carnauba wax, candelilla wax, bayberry wax, auricurry wax, espalt wax, etc.; animal waxes, e.g. bees wax, breached bees wax, insect wax, spermaceti, shellac, lanolin, etc; and the like. Of these preferred are carnauba wax, white beeswax and yellow beeswax.

Paraffin, petrolatum, microcrystalline wax, and the like, are given as specific examples of hydrocarbons, with preferable hydrocarbons being paraffin and microcrystalline wax.

Given as examples of higher fatty acids are caprilic acid, undecanoic acid, lauric acid, tridecanic acid, myristic acid, pentadecanoic acid, palmitic acid, malgaric acid, stearic acid, nonadecanic acid, arachic acid, heneicosanic acid, behenic acid, tricosanic acid, lignoceric acid, pentacosanic acid, cerotic acid, heptacosanic acid, montanic acid, nonacosanic acid, melissic acid, hentriacontanic acid, dotriacontanic acid, and the like. Of these, preferable are myristic acid, palmitic acid, stearic acid, and behenic acid.

Specific examples of higher alcohols are lauryl alcohol, tridecyl alcohol, myristyl alcohol, pentadecyl alcohol, cetyl alcohol, heptadecyl alcohol, stearyl alcohol, nonadecyl alcohol, arachyl alcohol, behenyl alcohol, carnaubic alcohol, corianyl alcohol, ceryl alcohol, and myricyl alcohol. Particularly preferable alcohols are cetyl alcohol, stearyl alcohol, and the like.

Specific examples of esters are fatty acid esters, e.g. myristyl palmitate, stearyl stearate, myristyl myristate, behenyl behenate, ceryl lignocerate, lacceryl cerotate, lacceryl laccerate, etc.; glycerine fatty acid esters, e.g. lauric monoglyceride, myristic monoglyceride, stearic monoglyceride, behenic monoglyceride, oleic monoglyceride, oleic stearic diglyceride, lauric diglyceride, myristic diglyceride, stearic diglyceride, lauric triglyceride, myristic triglyceride, stearic triglyceride, acetylstearic glyceride, hydoxystearic triglyceride, etc.; and the like. Glycerine fatty acid esters are more preferable.

Specific examples of metal salts of higher fatty acid are calcium stearate, magnesium stearate, aluminum stearate, zinc stearate, zinc palmitate, zinc myristate, magnesium myristate, and the like, with preferable higher fatty acid salts being calcium stearate and magnesium stearate.

These hydrophobic or water repellant components can be used either singly or in combination of two or more. These may be used in the following amounts, from about 0.01% to about 90% (w/w), but typically from about 0.5% to about 70% (w/w) of a coating composition.

An organosol polymeric coating composition or other coating composition may also contain other additives normally found in coatings used in the pharmaceutical art such as plasticizers, anti-tacking agents such as talc and coloring agents.

Examples of plasticizers include diethylphthalate, triethyl citrate, triethyl acetyl citrate, triacetin, tributylcitrate, polyethylene glycol, glycerol, vegetable and mineral oils.

Coloring agents are added for elegance and aesthetics or to differentiate products and may be chosen, for example, from metal oxide pigments or aluminum lake dyes.

A coating composition may include an anti-tacking agent such as talc. Other examples of suitable anti-tacking agent are calcium stearate, colloidal silicon dioxide, glycerin, magnesium stearate, and aluminum stearate.

In a specific example, an organosol polymeric coating is prepared by adding polymers, plasticizer, and anti-tacking agent to an organosolvent and mixed until homogenously dissolved or dispersed using a high shear mixer. The coating may be applied to a core particle using standard coating methodology. The organosol polymeric coating composition produces a strong continuous smooth film that adheres to the core.

As used herein, the term "active pharmaceutical ingredient" or "active pharmaceutical ingredients" refers to chemical or biological molecules providing a therapeutic, diagnostic, or prophylactic effect in vivo. Non-limiting active pharmaceutical ingredients contemplated for use in the compositions described herein include the following categories and examples of drugs and alternative forms of these drugs such as alternative salt forms, free acid forms, free base forms, and hydrates: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthamatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, pheneizine, desipramine, nortriptyline, tranylcypromine, fluoxetine, doxepin, imipramine, imipramine pamoate, isocarboxazid, trimipramine, venlafaxine, paroxetine, and protriptyline); antidiabetics (e.g., sulfonylurea derivatives); antifungal agents (e.g., griseofulvin, amphotericin B, nystatin, and candicidin); antihypertensive agents (e.g., propanolol, propafenone, oxyprenolol, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone); antiteoplastics (e.g., cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, and piposulfan); antianxiety agents (e.g., lorazepam, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, divalproex, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nisoldipine; and nitrates such as nitroglycerin, isosorbide dinitrate, pentaerythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, respiridone, and prochlorperazine); antimanic agents (e.g., lithium carbonate); antiarrhythmics (e.g., bretylium tosylate, esmolol, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillamine, salsalate, piroxicam, azathioprine, indomethacin, meclofenamate, gold sodium thiomalate, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibriolytic agents (e.g., aminocaproic acid); hemorheologic agents (e.g., pentoxifylline): antiplatelet agents (e.g., aspirin); anticonvulsants (e.g., valproic acid, divalproex sodium, phenyloin, phenyloin sodium, clonazepam, primidone, phenobarbitol, amobarbital sodium, methsuximide, metharbital, mephobarbital, mephenyloin, phensuximide, paramethadione, ethotoin, phenacemide, secobarbitol sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, loratadine, and); agents useful for calcium regulation (e.g., calcitonin, and parathyroid hormone); antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride. cloxacillin sodium, ticarcillin disodium, aziocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin) anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate, steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, glyburide, chlorpropamide, tolbutamide, and tolazamide); hypolipidemic agents (e.g., clofibrate, dextrothyroxine sodium, probucol, simvastatin, pravastatin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); oil-soluble vitamins (e.g., vitamins A, D, E, K, and the like); as well as other drugs such as mitotane, halonitrosoureas, anthrocyclines, and ellipticine.

A description of these and other classes of useful drugs and a listing of species within each class can be found in Martindale, The Extra Pharmacopoeia, 30th Ed. (The Pharmaceutical Press, London 1993).

Examples of other drugs useful in the compositions and methods described herein include ceftriaxone, ceftazidime, oxaprozin, albuterol, valacyclovir, urofollitropin, famciclovir, flutamide, enalapril, fosinopril, acarbose, lorazepan, follitropin, fluoxetine, lisinopril, tramsdol, levofloxacin, zafirlukast, interferon, growth hormone, interleukin, erythropoietin, granulocyte stimulating factor, nizatidine, perindopril, erbumine, adenosine, alendronate, alprostadil, benazepril, betaxolol, bleomycin sulfate, dexfenfluramine, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, nabumetone, trovafloxacin, dolasetron, zidovudine, finasteride, tobramycin, isradipine, tolcapone, enoxaparin, fluconazole, terbinafine, pamidronate, didanosine, cisapride, venlafaxine, troglitazone, fluvastatin, losartan, imiglucerase, donepezil, olanzapine, valsartan, fexofenadine, calcitonin, and ipratropium bromide. These drugs are generally considered to be water soluble.

Other drugs include albuterol, adapalene, doxazosin mesylate, mometasone furoate, ursodiol, amphotericin, enalapril maleate, felodipine, nefazodone hydrochloride, valrubicin, albendazole, conjugated estrogens, medroxyprogesterone acetate, nicardipine hydrochloride, zolpidem tartrate, amlodipine besylate, ethinyl estradiol, rubitecan, amlodipine besylate/benazepril hydrochloride, paroxetine hydrochloride, paclitaxel, atovaquone, felodipine, podofilox, paricalcitol, betamethasone dipropionate, fentanyl, pramipexole dihydrochloride, Vitamin D3 and related analogues, finasteride, quetiapine fumarate, alprostadil, candesartan, cilexetil, fluconazole, ritonavir, busulfan, carbamazepine, flumazenil, risperidone, carbidopa, levodopa, ganciclovir, saquinavir, amprenavir, carboplatin, glyburide, sertraline hydrochloride, rofecoxib carvedilol, halobetasolproprionate, sildenafil citrate, celecoxib, chlorthalidone, imiquimod, simvastatin, citalopram, ciprofloxacin, irinotecan hydrochloride, sparfloxacin, efavirenz, cisapride monohydrate, lansoprazole, tamsulosin hydrochloride, mofafinil, clarithromycin, letrozole, terbinafine hydrochloride, rosiglitazone maleate, lomefloxacin hydrochloride, tirofiban hydrochloride, telmisartan, diazapam, loratadine, toremifene citrate, thalidomide, dinoprostone, mefloquine hydrochloride, chloroquine, trandolapril, docetaxel, mitoxantrone hydrochloride, tretinoin, etodolac, triamcinolone acetate, estradiol. ursodiol, nelfinavir mesylate, indinavir, beclomethasone dipropionate, oxaprozin, flutamide, famotidine, prednisone, cefuroxime, lorazepam, digoxin, lovastatin, griseofulvin, naproxen, ibuprofen, isotretinoin, tamoxifen citrate, nimodipine, amiodarone, and alprazolam.

A controlled release delivery device of the present invention may be used for treatment of a patient, for example, an animal and more particularly, a mammal. By mammal, is meant any member of the class of mammalia that is characterized by being a vertebrate having hair and mammary glands. Examples include, without limitation, dog, cat, rabbit, horse, pig, goat, cow, human being. The delivery device of the present invention may be administered to any animal patient or mammalian patient that is in need of treatment with a site specific, timed, pulsed, chronotherapeutic, extended, or controlled release of an active ingredient. In one example, a delivery device of the present invention is used for treating a horse. In another example, a delivery device of the present invention is used for treating a human being.

The controlled release delivery device of the present invention may be used for the treatment of many human diseases, for example, without limitation, hypertension, angina, diabetes, HIV AIDS, pain, depression, psychosis, microbial infections, gastro esophageal reflux disease, impotence, cancer, cardiovascular diseases, gastric/stomach ulcers, blood disorders, nausea, epilepsy, Parkinson's disease, obesity, malaria, gout, asthma, erectile dysfunction, impotence, urinary incontinence, irritable bowel syndrome, ulcerative colitis, smoking, arthritis, rhinitis, Alzheimer's disease, attention deficit disorder, cystic fibrosis, anxiety, insomnia, headache, fungal infection, herpes, hyperglycemia, hyperlipidemia, hypotension, high cholesterol, hypothyroidism, infection, inflammation, mania, menopause, multiple sclerosis, osteoporosis, transplant rejection, schizophrenia, neurological disorders.

The core may be prepared by conventional techniques. The preferred technique is by dry or wet granulation of an active ingredient and excipients such as solubilizing agents, emulsifying agents, suspending agents, fillers, compression agents, stabilizers, pH altering agents, buffers, lubricants, and glidants.

Fillers, such as lactose, and compression agents such as microcrystalline cellulose, lubricants such as magnesium stearate and glidants such silicone dioxide may, in certain examples, be included in the core. The core onto which the coating is applied contains the active component. The core may be a tablet, capsule, caplet, pellet, spherical or irregular in shape.

In certain examples, swellable polymeric materials such as hydrogels that swell and expand significantly are not included in the core.

The extended release composition of the present invention can be any suitable size for drug delivery. Typically, the coated core weighs less than about 2 grams; from about 5 mg to about 1000 mg; from about 5 mg to about 500 mg; from about 5 mg to about 100 mg; from about 5 mg to about 30 mg; or from about 20 mg to 30 mg. The coated core may have a diameter of less than about 20 mm; from about 1 mm to about 10 mm; from about 1 mm to about 5 mm; or from about 2 mm to about 4 mm and a thickness that is less than about 20 mm; from about 1 mm to about 10 mm; from about 1 mm to about 5 mm; or from about 2 mm to about 4 mm. The coated core may be, for example, a tablet, pellet, mini-tablet, capsule and/or caplet. A plurality of coated cores may be combined and encapsulated in a capsule or made into a tablet or caplet.

Excipients may be homogenously mixed with an active ingredient in a core particle. Excipients may be selected from antiadherents, binders, diluents, emulsifying agents, suspending agents, compression agents, extrusion agents, pH altering agents, buffers, glidants, lubricants, solubilizers, wetting agents, surfactants, penetration enhancers, pigments, colorants, flavoring agents, sweetners, antioxidants, acidulants, stabilizers, antimicrobial preservatives and binders.

Excipients are biologically inert ingredients which enhance the therapeutic effect. The filler or diluent (eg lactose or sorbitol) is a bulking agent, providing a quantity of material which can accurately be formed into a tablet. The binders and adhesives (eg methyl cellulose or gelatin) hold the ingredients together so that they form a tablet and hold together. Lubricants (eg magnesium stearate or polyethylene glycol) are added to improve powder flow so that the die fills accurately, they also reduce the friction between the tablet and the machine so that the process progresses smoothly and uniformly.

Antiadherents are used to reduce the adhesion between the powder (granules) and the punch faces and thus prevent tablet sticking to the punches.

Binders hold the ingredients in a tablet together. Binders ensure that tablets and granules can be formed with required mechanical strength. Binders may be selected from starches, sugars, cellulose or modified cellulose such as hydroxypropyl cellulose, lactose, or sugar alcohols like xylitol, sorbitol or maltitol. Solution binders are dissolved in a solvent (for example water or alcohol and used in wet granulation processes. Examples of solution binders are gelatin, cellulose, cellulose derivatives, polyvinyl pyrrolidone, starch, sucrose and polyethylene glycol. Dry binders are added to a powder blend, either after a wet granulation step, or as part of a direct powder compression. Examples of dry binders are cellulose, methyl cellulose, polyvinyl pyrrolidone, polyethylene glycol. A commonly used binder or compression agent is microcrystalline cellulose. Microcrystalline and powdered cellulose products are sold under the tradenames Avicel™ PH (FMC Corporation, Philadelphia, Pa.) and Solka Floc™ (Penwest Company, Patterson N.Y.). Microcrystalline cellulose may be used in various techniques such as direct compression, dry granulation, wet granulation, or extrusion-spheronization.

Compression agents are materials that may be compacted. Compression agents may be added to increase the overall hardness of a core particle. Compression agents have inherently high compactibility due to properties of plastic deformation and limited elastic recovery. Non-limiting examples of materials that find use as compression agents are microcrystalline cellulose, silicified microcrystalline cellulose (for example Prosolv™ produced by JRS Pharma), oxidized polyethylene, calcium hydrogen phosphate dehydrate, dextrate, or sugar.

Fillers or diluents are added for bulk to fill out the size of a tablet or capsule, making it practical to produce and convenient for the consumer to use. Fillers/diluents are typically inert, compatible with the other components of the formulation, non-hygroscopic, soluble, relatively cheap, compactible, and preferably tasteless or pleasant tasting. Plant cellulose (pure plant filler) is a popular filler in tablets or hard gelatin capsules. Dibasic calcium phosphate is another popular tablet filler. A range of vegetable fats and oils can be used in soft gelatin capsules. Other examples of fillers include: lactose, sucrose, glucose, mannitol, sorbitol, and, calcium carbonate. Fillers/diluents are typically selected from microcrystalline cellulose, plant cellulose, calcium phosphate, mannitol, sorbitol, xylitol, glucitol, ducitol, inositiol, arabinitol; arabitol, galactitol, iditol, allitol, fructose, sorbose, glucose, xylose, trehalose, al lose, dextrose, altrose, gulose, idose, galactose, talose, ribose, arabinose, xylose, lyxose, sucrose, maltose, lactose, lactulose, fucose, rhamnose, melezitose, maltotriose, and raffinose. Preferred sugars include mannitol, lactose, sucrose, sorbitol, trehalose, glucose.

Glidants are used to improve the flowability of the powder or granules or both. Some examples of glidant(s) are silicon dioxide, starch, calcium silicate, Cabosil, Syloid, and silicon dioxide aerogels. Typically, silicon dioxide is used.

Lubricants prevent ingredients from clumping together and from sticking to the tablet punches or capsule filling machine. Lubricants also ensure that tablet formation and injection can occur with low friction between the solid and die wall. Some examples of lubricant(s) are alkali stearates such as magnesium stearate, calcium stearate, zinc stearate, polyethylene glycol, adipic acid, hydrogenated vegetable oils, sodium chloride, sterotex, glycerol monostearate, talc, polyethylene glycol, sodium benzoate, sodium lauryl sulfate, magnesium lauryl sulfate, sodium stearyl fumarate, light mineral oil and the like may be employed. Waxy fatty acid esters, such as glyceryl behenate, sold as "Compritol" products, can be used. Other useful commercial lubricants include "Stear-O-Wet" and "Myvatex TL". Common minerals like talc or silica, and fats, e.g. vegetable stearin, glycerol monostearate, magnesium stearate or stearic acid are typically used lubricants.

Sorbents are used for moisture-proofing by limited fluid sorbing (taking up of a liquid or a gas either by adsorption or by absorption) in a dry state.

Surfactants, wetting agents and solubilisers such as glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., TWEEN™), polyoxyethylene stearates, sodium dodecylsulfate, Tyloxapol (a nonionic liquid polymer of the alkyl aryl polyether alcohol type, also known as superinone or triton) is another useful solubilisers. Most of these solubilisers, wetting agents and surfactants are known pharmaceutical excipients and are described in detail in the Handbook of Pharmaceutical Excipients, published jointly by the American Pharmaceutical Association and The Pharmaceutical Society of Great Britain (The Pharmaceutical Press, 1986).

Preferred wetting agents include tyloxapol, poloxamers such as PLURONIC™ F68, F127, and F108, which are block copolymers of ethylene oxide and propylene oxide, and polyxamines such as TETRONIC™ 908 (also known as POLOXAMINE™ 908), which is a tetrafunctional block copolymer derived from sequential addition of propylene oxide and ethylene oxide to ethylenediamine (available from BASF), dextran, lecithin, dialkylesters of sodium sulfosuccinic acid such as AEROSOL™ OT, which is a dioctyl ester of sodium sulfosuccinic acid (available from American Cyanimid), DUPONOL™ P, which is a sodium lauryl sulfate (available from DuPont), TRITON™ X-200, which is an alkyl aryl polyether sulfonate (available from Rohm and Haas), TWEEN™ 20 and TWEEN™ 80, which are polyoxyethylene sorbitan fatty acid esters (available from ICI Specialty Chemicals), Carbowax 3550 and 934, which are polyethylene glycols (available from Union Carbide), Crodesta F-110, which is a mixture of sucrose stearate and sucrose distearate, and Crodesta SL-40 (both available from Croda Inc.), and SA90HCO, which is $C_8H_{37}$—$CH_2$ (CON($CH_3$)$CH_2$($CHOH$)$_4CF_{20}H$)$_2$.

Wetting agents which have been found to be particularly useful include Tetronic 908, the Tweens, Pluronic F-68 and polyvinylpyrrolidone. Other useful wetting agents include decanoyl-N-methylglucamide; n-decyl-.beta.-D-glucopyranoside, n-decyl-.beta.-D-maltopyranoside; n-dodecyl-.beta.-D-glucopyranoside, n-dodecyl.beta.-D-maltoside; heptanoyl-N-methylglucamide; n-heptyl-.beta.-D-glucopyranoside; n-heptyl-.beta.-D-thioglucoside; n-hexyl-.beta.-D-glucopyranoside; nonanoyl-N-methylglucamide; n-octyl-.beta.-D-glucopyranoside; octanoyl-N-methylglucamide; n-octyl-.beta.-D-glucopyranoside; and octyl-.beta.-D-thioglucopyranoside. Another preferred wetting agent is p-isononylphenoxypoly(glycidol), also known as Olin-10G or Surfactant 10-G (commercially available as 10G from Olin Chemicals). Two or more wetting agents can be used in combination.

The pharmaceutical composition or device may further include a pegylated excipient. Such pegylated excipients include, but are not limited to, pegylated phospholipids, pegylated proteins, pegylated peptides, pegylated sugars, pegylated polysaccharides, pegylated block-co-polymers with one of the blocks being PEG, and pegylated hydrophobic compounds such as pegylated cholesterol. Representative examples of pegylated phospholipids include 1,2-diacyl 1-sn-glycero-3-phosphoethanolamine-N-[Poly(ethylene glycol) 2000] ("PEG 2000 PE") and 1,2-diacyl-sn-glycero-3-phosphoethanolamine-N-[-Poly(ethylene glycol) 5000]("PEG 5000 PE"), where the acyl group is selected, for example, from dimyristoyl, dipalmitoyl, distearoyl, diolcoyl, and 1-palmitoyl-2-oleoyl.

Additional excipients may be included in the composition of the present invention. Further examples of excipients can include pigments, colorants, flavoring agents, preservatives and sweeteners. Flavors and colors are added to improve the taste or appearance of a formulation. Some typical preservatives used in pharmaceutical formulations are antioxidants such as vitamin A, vitamin E, vitamin C, and selenium, amino acids such as cysteine and methionine, citric acid and sodium citrate, or synthetic preservatives such as methyl paraben and propyl paraben. Sweeteners are added to make the ingredients more palatable, especially in chewable tablets such as antacid or liquids like cough syrup. Sugar may be used to disguise unpleasant tastes or smells.

One skilled in the art can select appropriate excipients for use in the composition of the present invention.

The core particle typically will not contain an excipient that is a swellable material such as a hydrogel in amounts that can swell and expand significantly so as to cause rupture or bursting of an organosol polymeric coat(s). Examples of swellable materials include hydrophilic polymers that are lightly cross-linked, such cross-links being formed by covalent or ionic bond, which interact with water and aqueous biological fluids and swell or expand to some equilibrium state. Swellable materials such as hydrogels exhibit the ability to swell in water and retain a significant fraction of water within its structure, and when cross-linked they will not dissolve in the water. Swellable polymers can swell or expand to a very high degree, exhibiting a 2 to 50 fold volume increase. Specific examples of hydrophilic polymeric materials that are typically absent from the core particle or present in amount that do not rupture or burst the organosol polymeric coat include poly(hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a water insoluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linking agent per mole of maleic anhydride in the copolymer, water-swellable polymers of N-vinyl lactams, cross-linked polyethylene oxides, and the like. Other examples of swellable materials include hydrogels exhibiting a cross-linking of 0.05 to 60%, hydrophilic hydrogels known as Carbopol™ acidic carboxy polymer, Cyanamer™ polyacrylamides, cross-linked water-swellable indene-maleic anhydride polymers, Good-rite™ polyacrylic acid, polyethyleneoxide, starch graft copolymers, Aqua-Keeps™ acrylate polymer, diester cross-linked polyglucan, and the like. Methods for testing swellable materials with regards to polymer imbibition pressure and hydrogel-water interface interaction are described in U.S. Pat. No. 4,327,725 issued May 4, 1982, titled "Osmotic device with hydrogel driving member". In certain examples, swellable polymeric materials such as hydrogels that swell and expand significantly are not included in the core particle. In other examples, the core particle comprises swellable polymeric materials such as hydrogels in amounts that do not result in rupture or bursting of an organosol polymeric coating that is applied directly to the core particle.

In an embodiment, the device is coated with a non-disintegrating and non-semi-permeable coat. Materials useful for forming the non-disintegrating non-semi-permeable coat are ethylcellulose, polymethylmethacrylates, methacrylic acid copolymers and mixtures thereof.

In yet another embodiment, the device is coated with a non-disintegrating semipermeable coat. Materials useful for forming the non-disintegrating semipermeable coat are cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. Other suitable polymers are described in U.S. Pat. Nos. 3,845,770, 3,916,899, 4,008,719, 4,036,228 and 4,612,008. The most preferred non-disintegrating semipermeable coating material is cellulose acetate comprising an acetyl content of 39.3 to 40.3%, commercially available from Eastman Fine Chemicals.

In an alternative embodiment, the non-disintegrating semipermeable or non-disintegrating non-semi-permeable coat can be formed from the above-described polymers and materials that will form pores or channels in the coat. The pore forming agents or channeling agents dissolve on contact with fluid and form passages through which fluid and active pharmaceutical ingredient(s) can move through the coat. The pore forming agent or channeling agent can be a water soluble material or an enteric material. Some general examples of pore forming agents or channeling agents are watersoluble materials such as cellulose ethers, polyethylene glycols or microcrystalline cellulose. Some further examples of pore forming agents or channeling agents are sodium chloride, potassium chloride, lactose, sucrose, sorbitol, mannitol, polyethylene glycol (PEG), for example PEG 600, polyvinyl pyrolidone, propylene glycol, hydroxypropyl cellulose, hydroxypropyl methycellulose, hydroxypropyl methycellulose phthalate, cellulose acetate phthalate, polyvinyl alcohols, methacrylic acid copolymers and mixtures thereof.

The active pharmaceutical ingredient(s) that are water soluble or that are soluble under intestinal conditions may also be used to create pores in the coat.

The pore forming agent comprises approximately 0 to about 75% of the total weight of the coating, most preferably about 0.5% to about 25% of the total weight of the coating. The pore forming agent dissolves or leaches from the coat to form pores in the coat for the fluid to enter the core and dissolve the active ingredient.

As used herein the term pore includes an aperture, orifice, bore, channel, hole, a discrete area of weakness or as created by soluble or leachable materials.

Polymeric coats may also be formed with commonly known excipients such as plasticizers and anti-tacking agents. Some commonly known plasticizers include adipate, azelate, enzoate, citrate, stearate, isoebucate, sebacate, dibutyl sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer, amounts of from 0 to about 25%, and preferably about 2% to about 20% of the plasticizer can be used based upon the total weight of the coating polymer. It will be understood that some polymeric coats may be formed without the use of a plasticizer, for example, without limitation, a polymeric coat of Eudragit NE30D™ (methacrylate copolymer).

An example of an anti tacking agent is talc. Depending on the coating polymer, amounts of from 0 to about 70%, and preferably about 10% to about 50% of talc can be used based upon the total weight of the coating polymer.

Generally, one or more coat layers around a core particle of the device will comprise from about 0.5% to about 70% and preferably about 0.5% to about 50% based on the total weight of the device with the coating. In certain examples, a core particle can be coated with from about 1 wt % to about 50 wt % of a polymeric coating based on the total weight of the coating and the core of the final product. More typically, the coating is from about 1 wt % to about 20 wt %, from about 1 wt % to about 10 wt %, from about 1 wt % to about 7 wt %, from about 3.5 wt % to about 7 wt %, from about 3.5 wt % to about 6 wt %, or from about 4 wt % to about 5 wt %. The coating is typically applied to the core to yield a surface area of less than about 100 mg/cm$^2$. The coating can be one or more layers.

In an alternative embodiment, the dosage form of the device may also comprise an effective amount of an active ingredient or an active pharmaceutical ingredient that is available for immediate release as a loading dose. This may be coated onto the coat of the device or it may be incorporated into the coat or it may be press coated into the coated device. The loading dose active ingredient may be the same or different than the active ingredient formulated in the core particle.

In the preparation of coated device, various conventional well known solvents may be used to prepare the device and apply the external coating to the device. In addition, various diluents, excipients, lubricants, dyes, pigments, dispersants etc. which are disclosed in Remington's Pharmaceutical Sciences, 1995 Edition may be used in the device.

In certain examples, active pharmaceutical ingredients are present in pharmaceutically effective amounts. An organosol polymeric coating composition is coated onto a core particle comprising the active ingredient in any conventional oral unit dosage form, such as a tablet, capsule, pill, granule or powder to form the desired preparation. The coating composition coats the core particle utilizing conventional methods known in the art. For example, the coating composition may coat the core in a fluidized bed or pan. Other examples include spraying or painting the composition onto the core particle; or immersing the core particle in the coating composition. Alternatively, the coating composition may be applied to the core particle, e.g., the drug pellets or tablets, in a fluid bed bottom spray coater by having the pellets or tablets suspended in an air stream, and a dispersion of the coating composition is sprayed thereon. Various conventional coating apparatuses may be employed to facilitate this including, for example, a centrifugal fluidized bed coating apparatus, a pan coating apparatus, or a fluidized bed granulating coating apparatus.

In one example, the coating layer is applied to the active core using bottom or top spray coating in a fluid bed coater until the desired coating thickness is obtained. In another example, the coating is applied to the active core using a side vented perforated coating pan. The coating is applied so as to substantially uniformly and rapidly contact and coat the core. It is preferred that the coating composition has substantially an uniform thickness around the core. The coat is applied to the core to yield a weight gain of about 0.1 to 50% and surface area of less than 25 mg per cm squared. The coating composition produces a strong continuous smooth film that adheres to the core.

In order to illustrate, and without limitation several typical forms of controlled release devices can be considered, for example, granules, tablets, capsules, spheroids, pellets, microspheres, nanospheres, microcapsules, crystals or other types of particles known to the skilled person comprising one or more of the following; active pharmaceutical ingredient; biological, chemical, nutraceutical, agricultural or nutritional materials; surrounded by one or more coats which is: a pharmaceutical dosage form having a core containing less than about 95% of active ingredient having a short half-life (less than 15 hours) which is coated with one or more coats and where the composition and size of the core and the composition and thickness of the coat or controls the site, time, rate and extent of release of the active ingredient from the dosage form:

(i) the core comprising of therapeutic amounts of one or more active ingredient, and one or more pharmaceutically acceptable excipient selected from solubulizing agents, emulsifying agents, suspending agents, fillers, compression agents, stabilizers, pH altering agents, buffers, lubricants, and glidants;

(ii) the core weighing less than 2 grams and is less than 20 mm in diameter and less than 20 mm in thickness;

(iii) the coating composition comprising less than 50% (w/w) one or more water insoluble organosoluble polymer and less than 50% (w/w) one or more water soluble hydrateable gel forming polymer;

(iv) the ratio of water soluble hydrateable gel forming polymer to water insoluble organosoluble polymer ranges from about 20:80 to about 60:40;

(v) the coat containing from 0 to 80% (W/W) of an active ingredient;

(vi) the polymers in the coating composition being dissolved in organosolvent such as ethanol;

(vii) the coating composition contain 1% to 50% (w/w) anti-tacking agent of the water insoluble organosoluble polymer;

(viii) the core being coated with the aforesaid coating composition such that when one or more coated cores undergo in-vitro dissolution testing between 0 to 60% is released in 1, 2, 3 or 4 hours, less than 110% is released in 5, 6, 7, 8, 9, 10, 11 or 12 hours and greater than 50% is released in 24 hours.

(ix) Optionally one or more coat contains or is made from a hydrophobic and or water repellant material chosen from Oil and fats, waxes, higher fatty acids, fatty acid esters, higher alcohols, hydrocarbons, and metal salts of higher fatty acids.

In certain examples, and for illustrative purposes only, there may be granules, tablets, capsules, spheroids, pellets, microspheres, nanospheres, microcapsules, crystals or particles other types of particles known to the skilled person surrounded by one or more coats which is: a pharmaceutical dosage form having;

(i) a core containing one or more first active ingredient, and one or more pharmaceutically acceptable excipient selected from solubulizing agents, emulsifying agents, suspending agents, fillers, compression agents, stabilizers, pH altering agents, buffers, lubricants, and glidants, made by dry or wet granulation and tableting techniques to form a tablet or by extrusion-spheronization or powder solution layering techniques to form active ingredient loaded beads;

(ii) the core is coated with a functional coating composition comprising of a plasticizer, anti-tacking agents, one or more water insoluble organosoluble polymer and one or more water soluble gel forming polymer prepared in an organosolvent wherein the water soluble polymer is present in an amount of 24% (w/w) to 84% (w/w) of the water insoluble organosoluble polymer on a dry basis;

(iii) the polymers in the coating composition being dissolved in organosolvent;

(iv) the coated core is optionally coated with a an additional functional coat that is pH sensitive;

(v) One or both coats optionally contain a second active ingredient that is the same or different than the one or more first active ingredient in the core;

(vi) An optional final coat containing a third active ingredient being applied to the coated core;

(vii) Optionally one or more coat contains or is made from a hydrophobic and or water repellant material chosen from Oil and fats, waxes, higher fatty acids, fatty acid esters, higher alcohols, hydrocarbons, and metal salts of higher fatty acids;

(viii) said coated core when subjected to in-vitro dissolution testing between 0 to 60% is released in 1, 2, 3 or 4 hours, less than 110% is released in 5, 6, 7, 8, 9, 10, 11 or 12 hours and greater than 50% is released in 24 hours.

Certain other examples pertain to a non-rupturing or non-bursting controlled release delivery device. One example is a non-rupturing controlled release delivery device for controlled release of an active ingredient consisting essentially of: (a) a core particle comprising the active ingredient and a suitable excipient homogenously dispersed or dissolved therein; and (b) a polymeric coat comprising a water soluble gel forming polymer and a water insoluble organosoluble polymer, the polymeric coat being applied directly to and substantially enveloping the core particle. Another example is a non-rupturing controlled release delivery device for controlled release of an active ingredient consisting essentially of: (a) a core particle comprising the active ingredient and a suitable excipient homogenously dispersed or dissolved therein; (b) a first polymeric coat comprising a homogenous mixture of a water soluble gel forming polymer and a water insoluble organosoluble polymer in a lower alkanol organosolvent; and (c) a second coat comprising a hydrophobic or water repellant material; wherein the first polymeric coat is applied directly to and substantially envelopes the core particle, the first polymeric coat does not comprise a latex dispersion, a matrix-type membrane, or regions of pore forming agents, and the core particle does not comprise a swellable polymeric material. Another example is a non-rupturing controlled release delivery device for controlled release of an active ingredient consisting essentially of:

(i) a core particle comprising the active ingredient and a suitable excipient homogenously dispersed or dissolved therein; and (ii) an organosol polymeric coat comprising a homogenous mixture of, (a) a water soluble gel forming polymer and a water insoluble organosoluble polymer in a dry weight ratio of from about 20:80 to about 50:50, (b) a lower alkanol organosolvent, and (c) an anti-tacking agent; the organosol polymeric coat being applied directly to and substantially enveloping the core particle. Another example is a controlled release delivery device for controlled release of an active ingredient consisting essentially of: (i) a core particle comprising the active ingredient and a suitable excipient homogenously dispersed or dissolved therein; (ii) an organosol polymeric coat comprising a homogenous mixture of, (a) a water soluble gel forming polymer and a water insoluble organosoluble polymer in a dry weight ratio of from about 20:80 to about 50:50, (b) a lower alkanol organosolvent, and (c) an anti-tacking agent, the organosol polymeric coat being applied directly to and substantially enveloping the core particle; and (iii) an aqueous coat comprising a water-soluble polymer, the aqueous coat functioning as a quick-dissolving coat; wherein the organosol polymeric coat does not comprise a latex dispersion, a matrix-type membrane, or regions of pore forming agents, and the core particle does not comprise a swellable polymeric material in an amount sufficient to cause rupture or bursting of the organosol polymeric coat.

When introducing elements disclosed herein, the articles "a", "an", "the", and "said" are intended to mean that there are one or more of the elements unless the context dictates otherwise. For example, the term "a compound" and "at least one compound" may include a plurality of compounds, including mixtures thereof. The terms "comprising", "having", "including" are intended to be open-ended and mean that there may be additional elements other than the listed elements.

The above disclosure generally describes the present invention. A more complete understanding can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

A controlled release tablet containing metoprolol succinate and having the following formula is prepared as follows:
1. Preparation of Core
Core Composition

| Ingredients | % |
| --- | --- |
| Metoprolol Succinate | 70.5 |
| Silicone dioxide | 1 |
| Lactose | 8 |
| Microcrystalline cellulose | 20 |
| Magnesium stearate | 0.5 |
| Water | q.s. |
| Total | 100 |

(a) Granulation

The metoprolol succinate, silicone dioxide, lactose and microcrystalline cellulose are added to a high shear granulator. This is granulated using water as the granulating. The wet granules are dried in an oven until the loss on drying is less than 5%. The dried granules are passed through a Comil equipped with the equivalent of a 16 mesh screen.

(b) Tableting

The magnesium stearate is blended with the granules for about five (5) minutes in aV-Blender. After blending, the granules are compressed to tablets using a rotary press.
2. Preparation of Coated Core
Ethylcellulose Coat Composition

| Ingredients | % w/w |
| --- | --- |
| Ethylcellulose | 8 |
| HPMC (E5LV) | 4.5 |
| Ethanol | 83.11 |
| Dibutylsebacate (DBS) | 1.89 |
| Talc | 2.5 |
| Total | 100 |

(a) Preparation and Application of Ethylcellulose Coat.

The ethylcellulose is dissolved in ethanol while stirring with a high shear mixer. The dibutyl sebacate, hydroxypropyl methyl cellulose and talc is added respectively while stirring under high shear until no lumps are seen. The coating suspension is then sprayed onto the core tablets in a perforated pan coater employing the following conditions: product temperature of 22 degree. C.; atomization pressure of about 40 psi; 14.5 g/min. The core tablet is coated to a theoretical weight gain of about 6%.

The core tablet may be seal coated with an Opadry material or other suitable water-soluble material by first dissolving the opadry material, preferably Opadry Clear, in purified water. The Opadry solution is then sprayed onto the core tablet using a pan coater under the following conditions: exhaust air temperature of 38-42.degree. C.; atomization pressure of 28-40 psi; and spay rate of 10-15 ml/min. The core tablet is coated with the sealing solution until a theoretical coating level of about 2% is obtained.

A dissolution experiment was done in a USP dissolution apparatus in water until an asymptote was reached and/or 24 hours had elapsed. Results are shown in FIG. 1.

Example 2

A controlled release tablet having a core containing methylphenidate and a coat is prepared as in example 1. To this is added a second coat having a coating formula prepared as follows:
Composition of Second (Enteric) Coat

| Eudragit L | 28.27 |
| --- | --- |
| Eudragit S | 3.14 |
| PEG | 6.28 |
| Talc | 15.70 |
| Water | 43.72 |
| Ethanol | 550.00 |

Preparation and Application of Second (Enteric) Coat.

This formulation is sufficient for coating 1200 g batch of the coated core. The Eudragits are blended under high shear in a vortex of ethanol. PEG and Talc are added to water while stirring under low agitation using a propeller mixer. Add the PEG-Talc mixture to the Eudragit mixture and stir for 45 minutes.

The coating solution is then sprayed onto the previously coated core tablets in a perforated coating pan coater employing the following conditions: product temperature of 27 degree. C.; atomization pressure of about 40 psi; 14.5 g/min. The core tablet is coated to a theoretical weight gain of about 4%.

Example 3

A controlled release pellet having a core containing venlafaxine as prepared in example 1.

Example 4

A controlled release pellet having a core containing paroxitine as prepared in example 1.

Example 5

A controlled release pellet having a core containing tramadol as prepared in example 1, to which is added an additional coat containing Naproxen prepared as follows:
Additional Quick Dissolving Coat Containing Naproxen

| Ingredient | (%) |
| --- | --- |
| Naproxen | 10 |
| Opadry II | 10 |
| Water | 80 |

The Opadry II is added to a vortex of water while stirring using a lightening mixer. Naproxen is added to the Opadry II suspension and stirred for 45 minutes. The coating suspension is then sprayed onto the Tramadol coated tablets in a perforated pan coater employing the following conditions: product temperature of 44 degree. C.; atomization pressure of about 40 psi; 14.5 g/min. The core tablet is coated to a theoretical weight gain sufficient to give the therapeutic amount of Naproxen required.

What is claimed is:

1. A method for providing controlled extended delivery of an active ingredient, said method comprising:
   administering controlled release delivery device for controlled release of said active ingredient to a subject, the controlled release delivery device comprising:
   (i) a core particle comprising the active ingredient homogenously dispersed or dissolved therein; and
   (ii) an organosol polymeric coat comprising a homogenous mixture of,
      (a) a water soluble gel forming polymer and a water insoluble organosoluble polymer in a dry weight ratio of from about 20:80 to about 50:50:
      (b) an organosolvent, and
      (c) an anti-tacking agent;
   the organosol polymeric coat being applied directly to and substantially enveloping the core particle.

2. The method of claim 1 for the treatment of hypertension, angina, diabetes, HIV AIDS, pain, depression, psychosis, microbial infections, gastro esophageal reflux disease, impotence, cancer, cardiovascular diseases, gastric/stomach ulcers, blood disorders, nausea, epilepsy, Parkinson's disease, obesity, malaria, gout, asthma, erectile dysfunction, impotence, urinary incontinence, irritable bowel syndrome, ulcerative colitis, smoking, arthritis, rhinitis, Alzheimer's disease, attention deficit disorder, cystic fibrosis, anxiety, insomnia, headache, fungal infection, herpes, hyperglycemia, hyperlipidemia, hypotension, high cholesterol, hypothyroidism, infection, inflammation, mania, menopause, multiple sclerosis, osteoporosis, transplant rejection, schizophrenia, or neurological disorders.

3. The method of claim 1, wherein the controlled release delivery device is administered by sprinkling on fruit, vegetable, or plant sauce.

4. The method of claim 1, wherein:
   (i) the core comprises less than about 95% of said active pharmaceutical ingredient (API) having a short half-life of less than 15 hours, and one or more pharmaceutically acceptable excipients selected from solubulizing agents, emulsifying agents, suspending agents, fillers, compression agents, stabilizers, pH altering agents, buffers, lubricants, and glidants;
   (ii) the core weighs less than 2 grams and is less than 20 mm in diameter and less than 20 mm in thickness; and
   (iii) the organosol polymeric coat is prepared from a coating composition that comprises less than 50% (w/w) one or more water insoluble organosoluble polymer and less than 50% (w/w) one or more water soluble gel forming polymer;
   (iv) wherein the ratio of water soluble hydrateable gel forming polymer to water insoluble organosoluble polymer ranges from about 20:80 to about 50:50;
   (v) wherein said organosol polymeric coat comprises from 0 to 80% (W/W) of an API;
   (vi) an organosolvent which is a lower alkanol;
   (vii) the organosol polymeric coating comprises 20% to 80% (w/w) anti-tacking agent of the water insoluble organosoluble polymer;
   (viii) the core being coated with the organosol polymeric coat such that when one or more coated cores undergo in-vitro dissolution testing between 0 to 60% is released in 1, 2, 3 or 4 hours, less than 110% is released in 5, 6, 7, 8, 9, 10, 11 or 12 hours and greater than 50% is released in 24 hours; and
   (ix) optionally, one or more organosol polymeric coat comprises or is made from a hydrophobic and or water repellant material chosen from oil, fats, waxes, higher fatty acids, fatty acid esters, higher alcohols, hydrocarbons, and metal salts of higher fatty acids.

5. The method of claim 4 wherein the controlled release delivery device is suspended in a suitable vehicle selected from water, paste, gel, suspension or an emulsion.

6. The method of claim 4, wherein the controlled release delivery device and the suitable vehicle are in a different housing and admixed prior to use.

7. The method of claim 1, wherein the organosol polymeric coat does not comprise a latex dispersion, a matrix-type membrane, or regions of pore forming agents, and the core particle does not comprise a swellable polymeric material in an amount sufficient to cause rupture or bursting of the organosol polymeric coat.

8. The method of claim 1, wherein the controlled release delivery device is compressed into tablets for oral administration.

9. The method of claim 1, wherein the administration is by suspending one or more of the controlled release delivery device in a suitable vehicle.

10. The method according to claim 1, wherein the organosolvent is a lower alkanol.

11. The method according to claim 1, wherein the organosolvent is selected from the group consisting of ethanol, 1-propanol, 2-propanol, 1-propen-3-ol (allyl alcohol), propylene glycol, glycerol, and 2-methyl-2-propanol.

12. The method according to claim 1, wherein the organosolvent is anhydrous ethanol.

13. The method according to claim 1, wherein the organosolvent is selected from the group consisting of dimethyl sulfoxide, diethyl sulfoxide, hexamethyl phosphoramide, pyruvic aldehyde dimethylacetal, and dimethylisosorbide.

14. The method according to claim 1, wherein the water soluble gel forming polymer is selected from the group consisting of hydroxyethyl cellulose, hydroxypropyl methylcellulose, methylcellulose, hydroxypropyl cellulose, carbomer, polyethylene glycol, polypropylene glycol, poloxamers, starch derivatives and polyvinylpyrrolidone.

15. The method according to claim 1, wherein the water soluble gel forming polymer is hydroxypropyl methylcellulose.

16. The method according to claim 1, wherein the water insoluble organosoluble polymer is selected from the group consisting of cellulose ether, cellulose ester, ethylcellulose, cellulose acetate, polymethacrylates, acrylate copolymer, methacrylate copolymer, and aminoalkyl methacrylate copolymer.

17. The method according to claim 1, wherein the water insoluble organosoluble polymer is ethylcellulose.

18. The method according to claim 1, dry weight ratio of the water soluble gel forming polymer to the water insoluble organosoluble polymer in the coating is from about 20:80 to about 45:55, from about 20:80 to about 40:60, from about 25:75 to about 50:50, from about 25:75 to about 45:55, or from about 25:75 to about 40:60.

19. The method according to claim 1, further comprising a coat comprising a pH sensitive polymer.

20. The method according to claim 1, the organosol polymeric coat further comprises a plasticizer.

21. The method of claim 1 for site specific, timed, pulsed, chronotherapeutic, or extended delivery of an active ingredient.

22. The method of claim 1, wherein one or more of the controlled release delivery device is suspended in a suitable vehicle for oral administration.

23. The method of claim 1, wherein the active ingredient is released after a lag time of not more than 12 hours.

24. The method of claim 1, wherein the active ingredient is one or more active pharmaceutical ingredients selected from drugs, or prodrugs or their salt forms, free acid forms, free base forms, Levo-, Dextro-, Dextro Levo-isomers, racemates, chiral forms, related compounds and hydrates.

25. The method according to claim 1, wherein said coated core when subjected to dissolution testing, less than 60% of the active ingredient is released in 1 hour, less than 80% is released in 6 hours and greater than 70% is released in 24 hours.

26. The method according to claim 1, wherein the organosol polymeric coat comprises from about 20 wt % to about 50 wt %, from about 20 wt % to about 45 wt %, from about 20 wt % to about 40 wt %, from about 25 wt % to about 50 wt % or from about 25 wt % to about 45 wt %, of the water insoluble organosoluble polymer.

27. The method according to claim 1, wherein the controlled release delivery device is non-rupturing or non-bursting.

28. The method according to claim 1, wherein the core particle is selected from granules, tablets, spheroids, pellets, microspheres, nanospheres, and crystals.

\* \* \* \* \*